(12) United States Patent
Meyer et al.

(10) Patent No.: US 7,869,855 B2
(45) Date of Patent: Jan. 11, 2011

(54) MEDICAL APPARATUS WITH RELEASABLE APPLICATOR

(75) Inventors: Peter F. Meyer, Shrewsbury, MA (US); Warren Copp-Howland, Chicopee, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 1065 days.

(21) Appl. No.: 11/528,912

(22) Filed: Sep. 28, 2006

(65) Prior Publication Data

US 2008/0081978 A1   Apr. 3, 2008

(51) Int. Cl.
*A61B 5/04* (2006.01)
(52) U.S. Cl. .............. 600/391; 600/323; 600/392; 600/595; 307/149; 307/152
(58) Field of Classification Search ............ 600/391, 600/392; 607/149, 152, 153
See application file for complete search history.

(56) References Cited

U.S. PATENT DOCUMENTS

| | | | | | |
|---|---|---|---|---|---|
| 3,774,592 | A | * | 11/1973 | Lahr | 600/392 |
| 4,777,954 | A | * | 10/1988 | Keusch et al. | 600/392 |
| 4,947,847 | A | * | 8/1990 | Nakao et al. | 600/391 |
| 5,263,481 | A | | 11/1993 | Axelgaard | |
| 5,265,579 | A | * | 11/1993 | Ferrari | 600/385 |
| 5,848,966 | A | | 12/1998 | Gusakov et al. | |
| 5,974,344 | A | | 10/1999 | Shoemaker, II | |
| 6,272,385 | B1 | * | 8/2001 | Bishay et al. | 607/142 |
| 6,745,062 | B1 | * | 6/2004 | Finneran et al. | 600/393 |
| 7,005,556 | B1 | | 2/2006 | Becker et al. | |

* cited by examiner

*Primary Examiner*—Lee S Cohen
(74) *Attorney, Agent, or Firm*—Lisa E. Winsor, Esq.

(57) ABSTRACT

A medical apparatus includes a substrate member and an applicator member. Substrate member includes a medical device and an adhesive layer for adhering to body tissue. Applicator member is releasably attached to the substrate member and is adapted for grasping by a clinician to facilitate application of the substrate member to body tissue.

17 Claims, 3 Drawing Sheets

MEDICAL APPARATUS WITH RELEASABLE APPLICATOR

BACKGROUND

1. Technical Field

The present disclosure generally relates to a medical apparatus and, more particularly, relates to a medical apparatus adapted to facilitate positioning of a substrate having diagnostic, therapeutic or monitoring capabilities, adjacent to body tissue.

2. Background of the Related Art

The natural contours of the human body often present difficulties to apply a therapeutic or diagnostic element to a skin surface. This difficulty is particularly compounded when the medical or therapeutic element is flexible. For example, clinicians often encounter difficulties when applying a medical electrode to a patient due to the flexibility of the substrate to which the electrode is attached and the presence of an adhesive surface.

Medical electrodes are often used to monitor bioelectric signals generated by the body. The electrodes may be covered in a conductive gel, which serves as an electrochemical coupling agent and enhances the ability of the electrode to adhere to a patient's skin. The electrodes may be connected to a monitoring system, processed and analyzed by medical personnel. The electrode devices further may include an adhesive pad and an electrically conductive member that is electrically connected to the monitoring system or an electromedical apparatus. However, due to the flexibility of the adhesive pads, many electrodes are often difficult to grasp and hard to position adjacent the wound.

SUMMARY

Accordingly, the present disclosure is directed to a medical apparatus including a substrate member and an applicator member. The substrate member includes a medical device and an adhesive layer for adhering to body tissue. The applicator member may be releasably attached to the substrate member and is adapted for grasping by a clinician to facilitate application of the substrate member to body tissue. The substrate member may be at least partially flexible. A protective member may be releasably secured to the adhesive layer. The protective member is removable prior to application of the substrate member to the body tissue.

The medical device may be selected from a group consisting of a sensor and a marker. In one embodiment, the medical device includes at least one electrode, and may include one or more electrodes on an electrode array. A sensor may include one of an accelerometer, thermal energy sensor, oxygen sensor, electromagnetic sensor and/or mechanical sensor. A marker may include one of a group consisting of LEDs, light bulbs, lamps and reflective devices.

The applicator member may be substantially flexible or alternatively rigid. The applicator member may be translucent. The applicator member further may include markings to facilitate the application of the medical device to the body tissue in the correct anatomical position. The applicator member also may include a handle. The applicator member may be removable from the substrate member after the substrate member is applied to body tissue.

The substrate member may have at least one substance with at least one property selected from a group consisting of antimicrobial properties, antibacterial properties and wound-treatment properties.

In an alternate embodiment, a medical apparatus includes a substrate member adapted for positioning adjacent to body tissue, a medical device engaged to the substrate member, and an applicator member mounted to the substrate member. The applicator member is adapted for grasping by a clinician to facilitate application of the substrate member to the body tissue. The applicator member is removable from the substrate member. An adhesive layer is disposed on one surface of the substrate member for attachment to the body tissue. The substrate member may be at least partially flexible. The applicator member may be substantially flexible or may be rigid. The applicator member may include a handle for facilitating manual engagement and manipulation by a clinician.

A method for performing a medical procedure is also disclosed. The method includes the steps of:

grasping an applicator member, the applicator member removably attached to a substrate, the substrate having a medical device adapted to perform a therapeutic or diagnostic medical procedure;

removing a protective layer to expose an adhesive layer of the substrate;

positioning the substrate on a body surface of a patient with the applicator member whereby the adhesive layer attaches the substrate to the body surface;

removing the applicator member from the substrate; and performing a medical procedure with the substrate.

BRIEF DESCRIPTION OF THE DRAWINGS

Preferred embodiments of the present disclosure are described hereinbelow with reference to the drawings, wherein.

DETAILED DESCRIPTION

Figure 1:
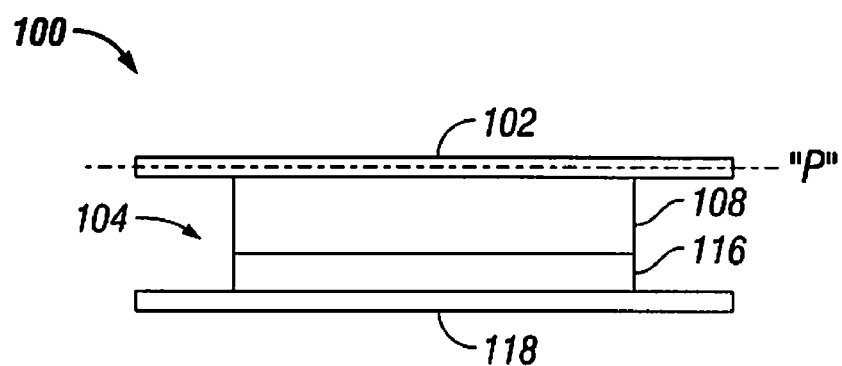
FIG. 1 is a side plan view of the medical apparatus in accordance with the principles of the present disclosure illustrating the applicator member and the substrate member.
Figure 2:
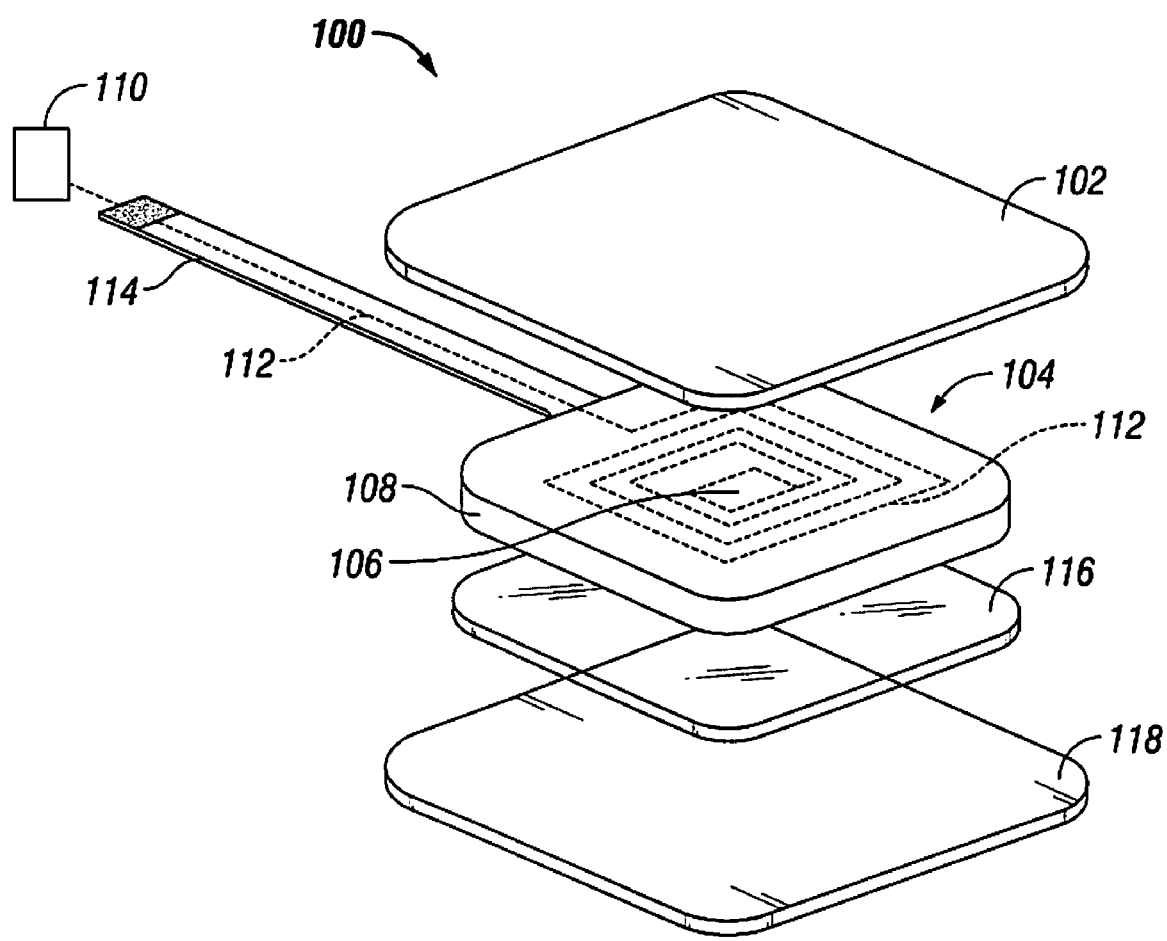
FIG. 2 is a perspective view with parts separated of the medical apparatus of FIG. 1.

Referring now to the drawings, in which like reference numerals identify identical or substantially similar parts throughout the several views, FIGS. 1-2 illustrate the medical apparatus 100 of the present disclosure. Medical apparatus 100 may be adapted to perform various medical procedures including therapeutic, diagnostic and/or monitoring surgical procedures, trans-cutaneous electrical nerve stimulation (TENS) or iontophoretic drug delivery. In one preferred embodiment, the medical apparatus 100 incorporates an electrode array and is a component of an electrical diagnostic or monitoring system. Other applications for medical apparatus 100 include wound closure elements, bandages, sensors, accelerators, markers, electrode arrays, and templates (to aid in the accurate placement of devices). Some possible sensors could include accelerometers, thermal energy sensors, oxygen sensors, electromagnetic sensors and mechanical sensors. Markers could include LEDs, light bulbs and reflective devices.

Medical apparatus 100 includes applicator member 102 and substrate member 104. Generally, applicator member 102 facilitates placement of substrate member 104 upon the patient, e.g., the epidermal tissue of the patient. Substrate member 104 preferably includes at least one therapeutic element, diagnostic element or other medical device 106 adapted to perform one of a diagnostic, therapeutic or monitoring surgical procedure as will be discussed.

Applicator member 102 is preferably releasably attached to substrate member 104. Means or methodologies for effecting such releasable attachment include, but, are not limited to adhesives, cements, hook and loop fasteners, tongue and groove mechanisms, bayonet couplings, perforations, break points and tear strips. Applicator member 102 may be translucent to permit or enhance visualization during application of substrate member 104 to the body tissue. Applicator member 102 may include anatomical reference indicators or markings to facilitate optimal anatomical placement on the patient's body. Applicator member 102 may be at least partially flexible or, alternatively, may be substantially rigid. If flexible, applicator member 102 may incorporate a flexible layer fabricated from, e.g., Mylar®, Tyvek®, or any other biaxially-oriented polyethylene terephthalate polyester films, Teslin® or any other polyolefin silica blend, natural woven fibers, synthetic non-woven material or paper. If rigid, applicator member 102 may be made from a polymeric material, stainless steel, titanium, wood, etc.

Substrate member 104 is constructed of a flexible material capable of generally conforming to the topography of a skin surface. Preferably, substrate member 104 is formed from a material which is sufficiently flexible and sufficiently strong to maintain its position on the patient. Suitable materials include Mylar®, Tyvek® or any other biaxially-oriented polyethylene terephthalate polyester films, Teslin® or any other polyolefin silica blend, natural woven fibers, synthetic non-woven material or paper. Substrate member 104 may include one or more substrate layers 108, materials and/or substances. For example, a substance in substrate layer 108, or additional material layer, may include antimicrobial properties, antibacterial properties and/or wound-treatment properties.

Therapeutic or diagnostic element 106 may be an electrode. Electrode 106 may be a component of an electrode array of electronic system (shown schematically as reference number 110) adapted to measure or collect data concerning electrical activity generated within the body. The type of electrode selected, and the placement of the electrode on the body, will determine the type of electrical activity measured. Any type of electrode known in the art may be used. Electronic system 110 may be any system known in the art capable of receiving electronic signals. In one preferred embodiment, electrode 106 is a component of an electronic system 110 used in the non-invasive monitoring of neurological or muscle activities, such as, for example, measuring maternal electrocardiogram, fetal electrocardiogram, and uterine muscle to ascertain the health and well being of the mother and fetus during labor, to characterize the progress of labor, or to predict the time of delivery of the fetus. Other applications of the electrode are also envisioned.

Electrically conductive trace or lead 112 may be in electrical contact with electrode 106 to electrically connect the electrode 106 with electronic system 108. Conductive trace 112 can be printed directly on substrate layer 108 if the substrate layer 108 is a dielectric. Various methods of printing include, but are not limited to, silk-screening, photoengraving, chemical etching, laser etching or mask electrodes. If substrate layer 108 is conductive, conductive trace 112 could be printed upon a separate dielectric substrate layer 108. In one embodiment, substrate layer 108 includes extension 114 upon which conductive trace 112 may be printed and, which leads to electronic system 110.

Referring still to FIGS. 1-2, substrate member 104 preferably further includes adhesive layer 116 for attachment of the substrate member 104 to the body surface and protective layer 118 which is removably attached to the adhesive layer 116. Adhesive layer 116 is in substantial contact with one surface of substrate layer 108. Adhesive layer 116 may contain electrolytes (such as electrode gel), pressure sensitive adhesives and/or adhesive gum. Adhesive layer 116 may include 3 dimensionally stable natural and/or synthetic polymers, such as cross-linked polyacrylamide. Adhesive layer 116 has a tacky surface which is adapted to adhere to the skin of the user and to provide reliable electrical contact therewith. Once applied to the skin, moisture, salt and heat from the body may be absorbed into adhesive layer 116, increasing the layer's adherence.

Protective layer 118 provides protection to the surface of adhesive layer 116 during packaging, shipping and storage to prevent drying of the adhesive layer 116 and any of the gels, electrolytes, etc. incorporated into the adhesive layer 116. Protective layer 118 may be constructed from a variety of different materials, including, but not limited to, flexible plastic, silicone-coated Mylar®, Tyvek® or other polymeric materials, or silicone-coated paper.

In use of the medical apparatus 100 of FIGS. 1-2, the body surface is prepared as is conventional. The clinician grasps applicator member 102 with one hand and removes protective layer 118 to thereby expose adhesive layer 116. With the use of applicator member 102, the clinician applies substrate member 104 to the surface of the body whereby adhesive layer 116 readily attaches to the skin surface. Once secured to the skin surface, the clinician removes applicator member 102 from substrate member 104 by releasing the attachment mechanism couplings, tongue and groove mechanisms or hook and loop fasteners, the mechanical connection is released followed by removal of the applicator member 102. If the applicator member 102 is releasably secured to substrate member 104 with an adhesive or cement, the adhesive connection is released subsequent to attachment of the substrate member 104 to the body surface. Preferably, the force required to overcome the adhesive connection of applicator member 102 to substrate member 104 is less than the force required to separate the substrate member 104 from the body tissue.

Clinician then performs a medical procedure with medical device (e.g., electrode) 106 of substrate member 104. The medical procedure may be a therapeutic procedure, a diagnostic procedure, a monitoring procedure, such as, for example, electrically connecting a conductive lead to substrate layer 108 and transmitting an electrical signal to a monitoring device. Medical procedure may be transcutaneous electrical nerve stimulation for the treatment of low back pain (LBP), myofascial and arthritic pain, sympathetically mediated pain, bladder incontinence, neurogenic pain, visceral pain, and postsurgical pain. Medical procedure may include the delivery of drugs, such as, for example, an iontophoretic drug delivery procedure.

Figure 3:
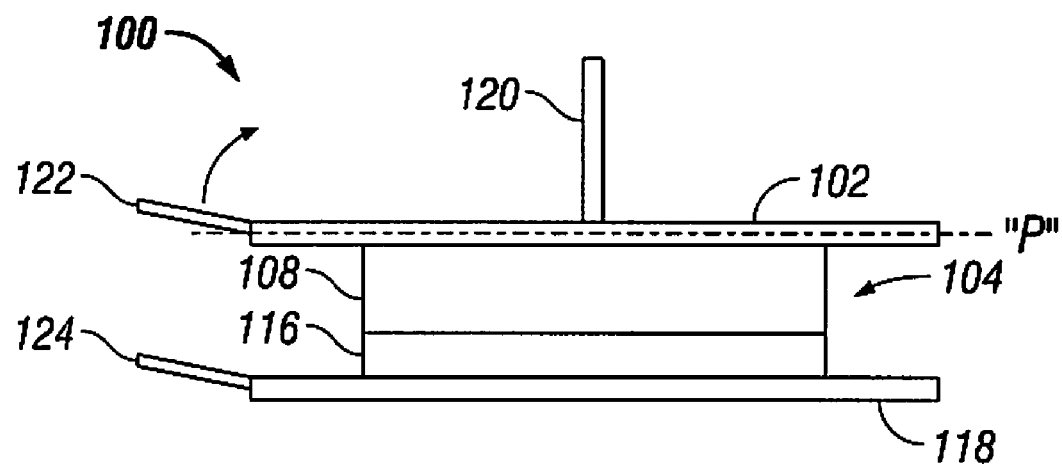
FIG. 3 is a side plan view of an alternate embodiment of the medical apparatus incorporating a handle.

FIG. 3 illustrates an alternate embodiment of medical apparatus 100. In accordance with this embodiment, applicator member 102 includes rigid handle 120 connected to an upper surface of the applicator member 102. Handle 120 may be securely connected to, e.g., monolithically formed with, applicator member 102 or may be releasably mounted to the applicator member 102 via any of the aforementioned mechanical or adhesive means. Handle 120 further facilitates application of substrate member 104 to the body surface by providing a means by which the clinician may readily grasp applicator member 102 and manipulate the applicator member 102 to a desired orientation relative to the body surface. For example, handle 120 may traverse or intersect a reference plane "p" defined by substrate member 104. In one embodiment, handle 120 is in orthogonal relation to the reference plane "p". Moreover, handle 120 enables the clinician to directly apply a predetermined level of force to substrate member 104 to ensure adhesive layer 116 of the substrate member 104 contacts a sufficient area of the body surface. Handle 120 may be translucent. Once substrate member 104 is applied to the body surface, applicator member 102 may be removed from the substrate member 104 via handle 120.

Applicator member 102 may incorporate tab 122 to further facilitate removal of the applicator member 102 subsequent to the placement of substrate member 104 to the body surface. Tab 122 is dimensioned to be manually engaged by the clinician and may be rigid or flexible and, may or may not be integrally formed with applicator member 102. Tab 122 may traverse the reference plane "p" of substrate member 104, and may be obliquely arranged relative to the reference plane "p". Tab 122 permits a twisting action to be applied to applicator member 102 to remove the applicator member. Handle 120 and tab 122 may be used individually or in combination to remove applicator member 102.

With further reference to FIG. 3, protective layer 118 may incorporate a tab 124 to facilitate removal of the protective layer 118 prior to application of substrate member 104 to the body surface.

Figure 4:
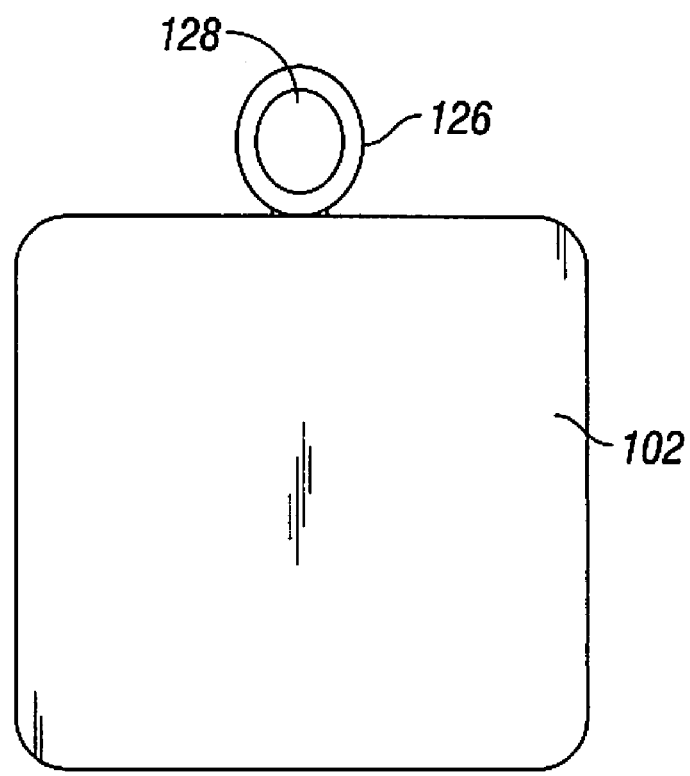
FIG. 4 is top plan view of an alternate embodiment of the applicator member.

FIG. 4 illustrates another alternative embodiment of the medical apparatus 100. In accordance with this embodiment, applicator member 102 incorporates loop or key ring tab 126. Loop 126 may be monolithically formed with applicator member 102 or it may be attached to applicator member 102 via any of the aforementioned mechanical or adhesive means. Loop 126 defines opening 128 for receiving the clinician's finger. In all other respects, applicator member 102 is used to apply substrate member 104 in substantially the same manner as described hereinabove.

Figure 5:
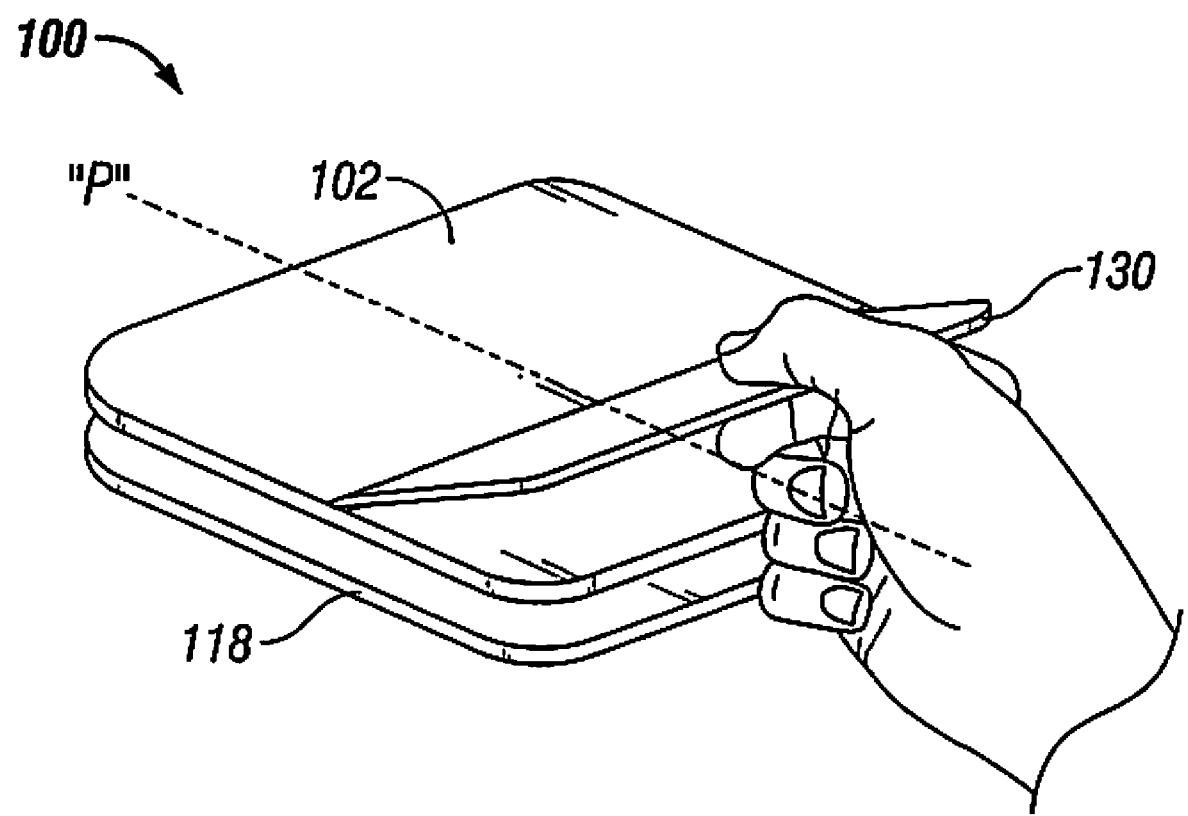
FIG. 5 is an elevated perspective view of an alternate embodiment of the applicator member.

FIG. 5 illustrates applicator member 102 with angular tab or fold 130 which depends from an intermediate portion of the applicator member 102, and may be in oblique relation to the reference plane "p" of the substrate member 104. Angular tab or fold 130 is arranged to be readily grasped by clinician to facilitate removal of the applicator member as shown in the FIG. 5.

It is envisioned that any or all of the components of apparatus 100 could be oxygen or liquid permeable. Substances having anti-microbial or anti-bacterial properties could be stored within any of the components to facilitate tissue healing. Perforations could be included within certain layers in order to distribute medicinal substances therethrough. Moreover, some or all of the layers could be partly or wholly translucent providing additional visibility.

Applicator member 102 may take on a variety of different shapes, sizes and designs. Some possible shapes could include, but are not limited to, square, circular, oval, triangular, oblong, polygonal and rectangular. Moreover, the shapes of each layer could differ. For example, the adhesive layer and substrate could be circular while the protective and applicator layers are square.

It will be understood that various modifications can be made to the embodiments of the present invention herein disclosed without departing from the spirit and scope thereof. Therefore, the above description should not be construed as limiting the invention but merely as exemplifications of embodiments thereof. Those skilled in the art will envision other modifications within the scope and spirit of the present invention as defined by the claims appended hereto.

What is claimed is:

1. A medical apparatus, which comprises:
   a substrate member including opposed upper and lower surfaces and opposed longitudinal ends, and defining a reference plane extending between the longitudinal ends, the substrate member including a medical device and having an adhesive layer adjacent the lower surface for adhering to body tissue; and
   an applicator member releasably attached to the upper surface of the substrate member, the applicator member having a grasping segment depending at least radially outwardly relative to the reference plane to traverse the reference plane to define first and second opposing grasping surfaces, the first and second opposing grasping surfaces dimensioned and arranged to be engaged by a clinician during application of the substrate member to body tissue, the applicator member being releasable subsequent to disposition of the adhesive layer to the body tissue.

2. The medical apparatus according to claim 1 wherein the substrate member is an at least partially flexible.

3. The medical apparatus according to claim 1 including a protective member releasably secured to the adhesive layer, the protective member being removable prior to application of the substrate member to the body tissue.

4. The medical apparatus according to claim 1 where the medical device is selected from a group consisting of a sensor and a marker.

5. The medical apparatus according to claim 4, wherein the sensor includes one of an accelerometer, thermal energy sensor, oxygen sensor, electromagnetic sensor and/or mechanical sensor.

6. The medical apparatus according to claim 4, wherein the marker includes one of a group consisting of LEDs, light bulbs, lamps and reflective devices.

7. The medical apparatus according to claim 1 wherein the medical device includes at least one electrode.

8. The medical apparatus according to claim 1 wherein the medical device includes one or more electrodes on an electrode array.

9. The medical apparatus according to claim 1 wherein the applicator member is substantially flexible.

10. The medical apparatus according to claim 1 wherein the substrate member includes an intermediate segment disposed between the opposed longitudinal ends thereof and wherein the grasping segment of the applicator member is arranged to depend outwardly from a position adjacent the intermediate segment and spaced from the opposed longitudinal ends.

11. The medical apparatus according to claim 10 wherein the grasping segment is arranged in oblique relation to the reference plane.

12. The medical apparatus according to claim 10 wherein the grasping segment includes a handle, the handle extending in substantial orthogonal relation to the reference plane.

13. The medical apparatus according to claim 10 wherein the medical device is selected from a group consisting of a sensor and a marker.

14. The medical apparatus according to claim 10 wherein the medical device includes at least one electrode.

15. The medical apparatus according to claim 1 wherein the grasping segment includes a loop defining an opening for receiving the clinician's finger.

16. A medical apparatus, which comprises:
- a substrate member including opposed upper and lower surfaces and defining a periphery;
- at least one of an electrode or sensor mounted adjacent the lower surface of the substrate member;
- an adhesive layer adjacent the at least one of an electrode or sensor for adhering to body tissue; and
- an applicator member releasably attached to the upper surface of the substrate member, the applicator member having a finger loop defining an opening for reception of a finger of a clinician, the finger loop extending beyond the periphery of the substrate member to facilitate access thereto, the applicator member being releasable subsequent to disposition of the adhesive layer to the body tissue.

17. The medical apparatus according to claim 16 wherein the finger loop is arranged to traverse a reference plane defined by the substrate member.

* * * * *